US00PP28893P2

(12) United States Plant Patent
Horvath

(10) Patent No.: US PP28,893 P2
(45) Date of Patent: Jan. 23, 2018

(54) ***GEUM* PLANT NAMED 'CITRONGE'**

(50) Latin Name: ***Geum* hybrid**
Varietal Denomination: Citronge

(71) Applicant: Brent Horvath, Fontana, WI (US)

(72) Inventor: Brent Horvath, Fontana, WI (US)

( * ) Notice: Subject to any disclaimer, the term of this patent is extended or adjusted under 35 U.S.C. 154(b) by 134 days.

(21) Appl. No.: 14/756,506

(22) Filed: Sep. 14, 2015

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
*Assistant Examiner* — Karen Redden

(57) ABSTRACT

A new, distinct *Geum* plant as shown and described, characterized by single orange flowers RHS color 24 B with wavy petals that overlap.

1 Drawing Sheet

Latin name: *Geum* hybrid.
Cultivar name: 'Citronge'.

BACKGROUND OF THE INVENTION

The present invention relates to a new and distinct hybrid of *Geum* plant named 'Citronge' characterized by single orange flowers with wavy petals that overlap. The new *Geum* was developed as an open pollinated seedling as part of a breeding and selecting program, at a nursery owned by the inventor in Helbron, IL. in 2008. The selection of the new plant was due to its' single orange flowers with wavy petals that overlap. The initial asexual propagation of the new plant was by division and took place at a nursery in Hebron, IL. in 2009. Continued asexual propagation by division since that time has shown that the unique features of this new *Geum* plant are stable and reproduced true to type in successive generations.

SUMMARY OF THE INVENTION

In the following description, color references are made to The Royal Horticultural Society Colour Chart (2001). The new *Geum* plant named 'Citronge' is characterized by single orange flowers RHS 24 B with wavy petals that overlap.

The new *Geum* plant can be compared to 'Sea Breeze' U.S. Plant Pat. No. 26,437, flower colors are deep orange flowers of RHS 34 A while the new plant flower color is orange RHS 24 B. Flowers of 'Sea Breeze' also grow wider to 50 mm compared to the new plant flower width of 30 mm.

The new plant can also be compared to *Geum* 'Totally Tangerine' U.S. Plant Pat. No. 22,041, which is a sterile hybrid with lighter orange single flowers of 32 A, that fades to 169 C. Plants of *Geum* 'Totally Tangerine' also grow to 130 cm tall while the new plant only grows 33 cm tall at maturity.

The new plant can also be compared to *Geum* 'Limoncello' not patented, which has bright yellow single flowers of 9 A while the new plant flower color is orange RHS 24 B.

Plants of *Geum* 'Limoncello' grow shorter to 30 cm tall while the new plant grows 33 cm tall at maturity.

DESCRIPTION OF PHOTOGRAPHS

Figure 1:
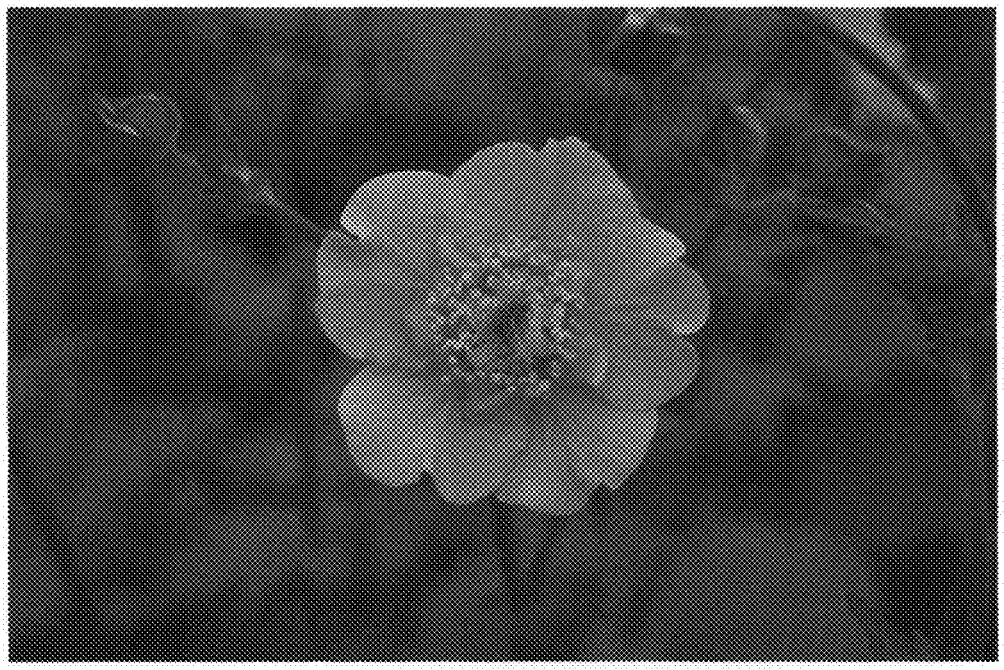

FIG. 1. Close up of the flower on an 8 month old plant in Hebron, IL USA.

Figure 2:
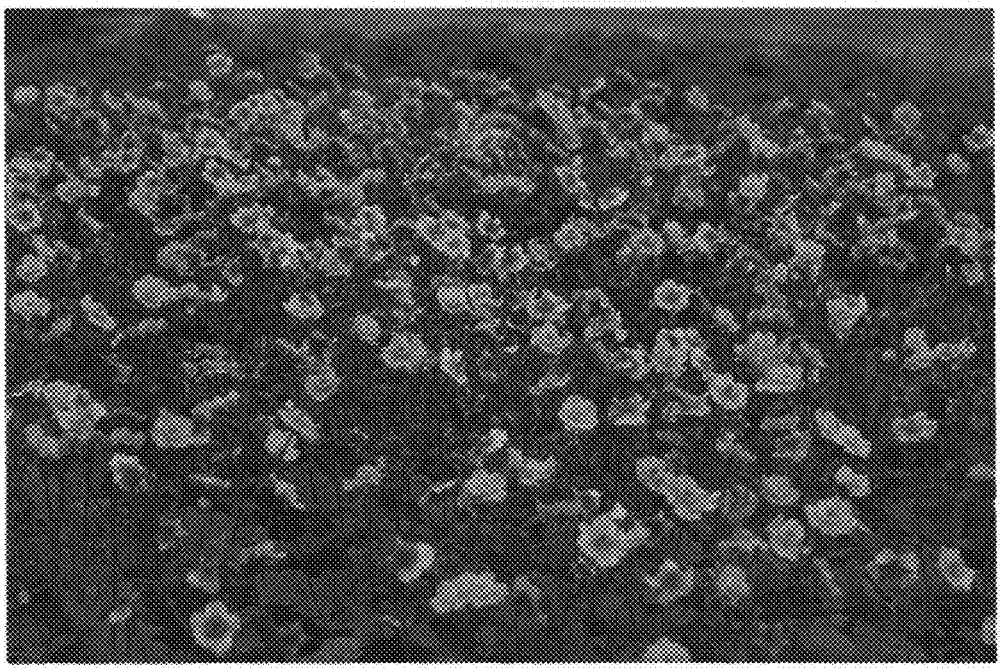

FIG. 2. One gallon, Blooming plants in May on an 8 month old plant in Hebron, IL USA.

DETAILED BOTANICAL DESCRIPTION

In the following description, color references are made to The Royal Horticultural Society Colour Chart (2001). Plants used for the description were grown in a 3 gallon container for two years at a nursery in Hebron, IL. Measurements and numerical values represent averages of typical plants.

Botanical classification: *Geum* hybrid cultivar 'Citronge'.

Parentage: Unknown.

Propagation: Vegetative division, vegetative unrooted cuttings taken in June in Hebron, IL USA, initiate roots in 4 weeks.

Roots: Fibrous, color close to 155 A.

Plant description: Overall habit of the new *Geum* is basal clumps, with medium vigor, upright red stems color 183 B with single orange flowers RHS 24 B with wavy petals that overlap.

*Plant type*.—Herbaceous perennial.

*Plant height*.—33 cm.

*Plant width*.—30 cm.

*Stem*.—Diameter: 4 mm.

*Stem or basal branches*.—Length up to 33 cm, with the internode between basal foliage and first leaflet length being 6 cm and the second internode between the first leaflet and the second leaflet length being 7 cm and the third internode between the second and third leaflet length being 6 cm and the fourth internode between the third and fourth leaflet length being 6 cm.

*Stem coloration*.—183 B.

Foliage description:

*Type*.—Herbaceous.

*Arrangement*.—Basal alternate with typically two or three lateral leaflets per stem.

*Petiole*.—Up to 18 cm long, with a diameter of 4 mm, color is 146 C, pubescent.

*Terminal compound leaf length*.—Up to 15 cm.

*Terminal compound leaf width*.—6 cm.

*Terminal leaflet length*.—Typically 3 cm.

*Terminal leaflet width*.—Typically 2 cm.
*Terminal leaflet shape*.—Obovate with incised margins.
*Terminal and lateral leaf apex*.—Acute.
*Terminal and lateral leaf base*.—Cuneate.
*Terminal and lateral leaf margin*.—Incised.
*Texture*.—Terminal and lateral leaf, upper and lower surfaces: pubescent.
*Stipules*.—None observed.
*Venation pattern*.—Terminal and lateral leaf, upper and lower surfaces: pinnate.
*Venation color*.—Terminal and lateral leaf, upper surface is color 137 B and lower surface color is 146 D.
*Lateral leaflet number*.—3 per stem.
*Lateral leaflet length*.—2 cm.
*Lateral leaflet width*.—Up to 2 cm.
*Lateral leaflet shape*.—Obovate.
*Adaxial leaf description*.—Color is close to 137 C.
*Abaxial leaf description*.—Color is close 146 B.

Flower description:

*Flower type*.—Corymb.
*Flower color*.—Orange RHS 24 B on top and 23 C on the bottom.
*Flower size*.—Diameter: 40 mm across, depth 20 mm.
*Flower number*.—4-5 per stem, 120 per plant.
*Number flowering stems*.—28.
*Bloom period and duration*.—Beginning the first week of May into the first week of June in Hebron, IL.
*Flower longevity and duration on the plant*.—Approximately 3 weeks.
*Flower longevity and duration cut*.—Approximately one week.
*Individual flower duration*.—Approximately 2 weeks with petals eventually drying to a tan color.
*Scent*.—None.
*Petal count*.—5.
*Petal shape*.—Spatulate.
*Petal arrangement*.—Rotate, overlapping, unfused.
*Petal longevity*.—Self-cleaning.
*Petal diameter or width*.—19 mm across and petal length — 16 mm long.
*Petal apex*.—Retuse, base: attenuate, margin: entire.
*Petal texture*.—Upper and lower surfaces: smooth, glabrous.
*Petal color*.—Upper surface is color 24 B.
*Petal color*.—Lower surface color is 23 C.
*Overall corymb size*.—Diameter and height — 6 cm across, 5 cm long.
*Flower buds*.—Diameter: 13 mm across, depth: 14 mm, shape: ovoid, surface: slightly pubescent and color is 183 B.
*Sepal size*.—Length: up to 13 mm, diameter: 8 mm at base coming to a point.
*Sepal quantity*.—5, fused at the base.
*Sepal shape*.—Lanceolate, apex: acute, base: cuneate, margin: entire.
*Sepal texture*.—Upper and lower surfaces: Pubescent.
*Sepal color*.—Adaxial color N 144 A. Abaxial color close to 183 B.
*Peduncle color and texture*.—The red parts are 183 B the green parts are 1443C, pubescent.
*Peduncle size*.—Length: 23 mm, diameter: 3 mm, Pedicel texture — pubescent.
*Pedicel size*.—Length: 2-3 mm, diameter: 1-2 mm and color 183 B.
*Reproductive organs*.—Stamen — quantity over 100, length 4 mm.
*Anther*.—Quantity: over 100, length: 1 mm, diameter: close to 1 mm wide.
*Anther color*.—Between 15 A and B, Filament color — 23 B.
*Pollen*.—Typically present, color: 15 A and B.
*Stigma*.—Number over 50, width less than 1 mm, color 24 A.
*Style*.—Number: over 50, length: 5 mm, shape — linear, color — 24 A.
*Pistil*.—Number: over 50, length: 9-10 mm, diameter — 5 mm wide, color — tips 9 A, base 145 A.
*Ovaries*.—Number: over 50 per bloom average, color: is 145 A.
*Fruit and seed*.—Number: over 50 per bloom average, color: is brown, 200 A, tear shaped, length — 9 mm, width — 2 mm. Seed — length 9 mm, width 2 mm, color-151 B, texture — pubescent.
*Hardiness*.—USDA zone 4 to 9.

Disease resistance: Resistance to diseases common to *Geum* has not been observed on plants grown under nursery conditions.

I claim:

1. A new, distinct *Geum* plant as shown and described, characterized by single orange flowers RHS color 24 B with wavy petals that overlap.

* * * * *